United States Patent [19]

Owen et al.

[11] Patent Number: 5,377,004
[45] Date of Patent: Dec. 27, 1994

US005377004A

[54] REMOTE OPTICAL MEASUREMENT PROBE

[75] Inventors: Harry Owen, Ann Arbor; James M. Tedesco, Livonia; Joseph B. Slater, Ypsilanti, all of Mich.

[73] Assignee: Kaiser Optical Systems, Ann Arbor, Mich.

[21] Appl. No.: 137,851

[22] Filed: Oct. 15, 1993

[51] Int. Cl.$^5$ .................. G01J 3/44; G01N 21/65; G01N 21/64
[52] U.S. Cl. .................. 356/301; 250/458.1; 356/318
[58] Field of Search ............ 356/301, 317, 318, 417; 250/458.1, 459.1, 461.1, 461.2

[56] References Cited

U.S. PATENT DOCUMENTS 5,112,127  5/1992  Carrabba et al. ............... 356/301
5,166,813  11/1992  Metz ........................... 250/458.1

OTHER PUBLICATIONS

Barbillat, J.; Delhaye, M.; Dhamelincourt, P.j "Confocal Raman Mapping", pp. 1514–1515, 1992.
Dilar Raman Probe Brochure, undated.

*Primary Examiner*—F. L. Evans
*Attorney, Agent, or Firm*—Krass & Young

[57] ABSTRACT

A holographic probe facilitates the measurement of radiative effects such as Raman scattering or fluorescence of a remotely disposed sample. Improving upon prior-art techniques, the probe teaches a substantially in-line path between the sample and an output optic wherein a narrowband reflective element, preferably holographically recorded, is used to fold excitation energy from an illumination path into the collection path and reject any Rayleigh scattering received from the sample. The improved configuration further allows a dispersive filtering element to be placed in the illumination path, which may be used in conjunction with spatial filtering to reject non-excitation wavelengths.

13 Claims, 5 Drawing Sheets

REMOTE OPTICAL MEASUREMENT PROBE

FIELD OF THE INVENTION

The present invention relates generally to the measurement of optical effects such as Raman scattering and fluorescence of a remotely disposed sample and, in particular, to a probe which receives excitation energy from a first optical fiber, delivers the excitation energy to a sample under characterization, and couples scattered radiation to a second optical fiber while removing undesired wavelengths in both directions using holographic optical elements.

BACKGROUND OF THE INVENTION

Induced radiative effects such as Raman scattering and fluorescence have become extremely valuable tools associated with the non-destructive determination of molecular constituents. To characterize a composition in a remote or hostile environment, optical fibers may advantageously be used to deliver excitation energy to a sample under investigation and to carry scattered radiation back to means for spectral analysis. An excitation source path may take the form of a laser providing a stimulus at an appropriate wavelength coupled to an input fiber, and a collection path may be made up of a second fiber carrying return radiative information to a spectral analysis tool such as a spectrograph.

Such remote spectral analysis presents technical challenges, however, including the strong scattering signature of the material used for the optical fiber, this interference potentially being generated by both the laser excitation in the illumination fiber and any strong Rayleigh (unshifted) Scattering allowed to enter the collection fiber. These spurious fiber signatures can compete with, or even overshadow, the desired signature of the sample under test, particularly when long lengths of fiber are used.

Figure 1:
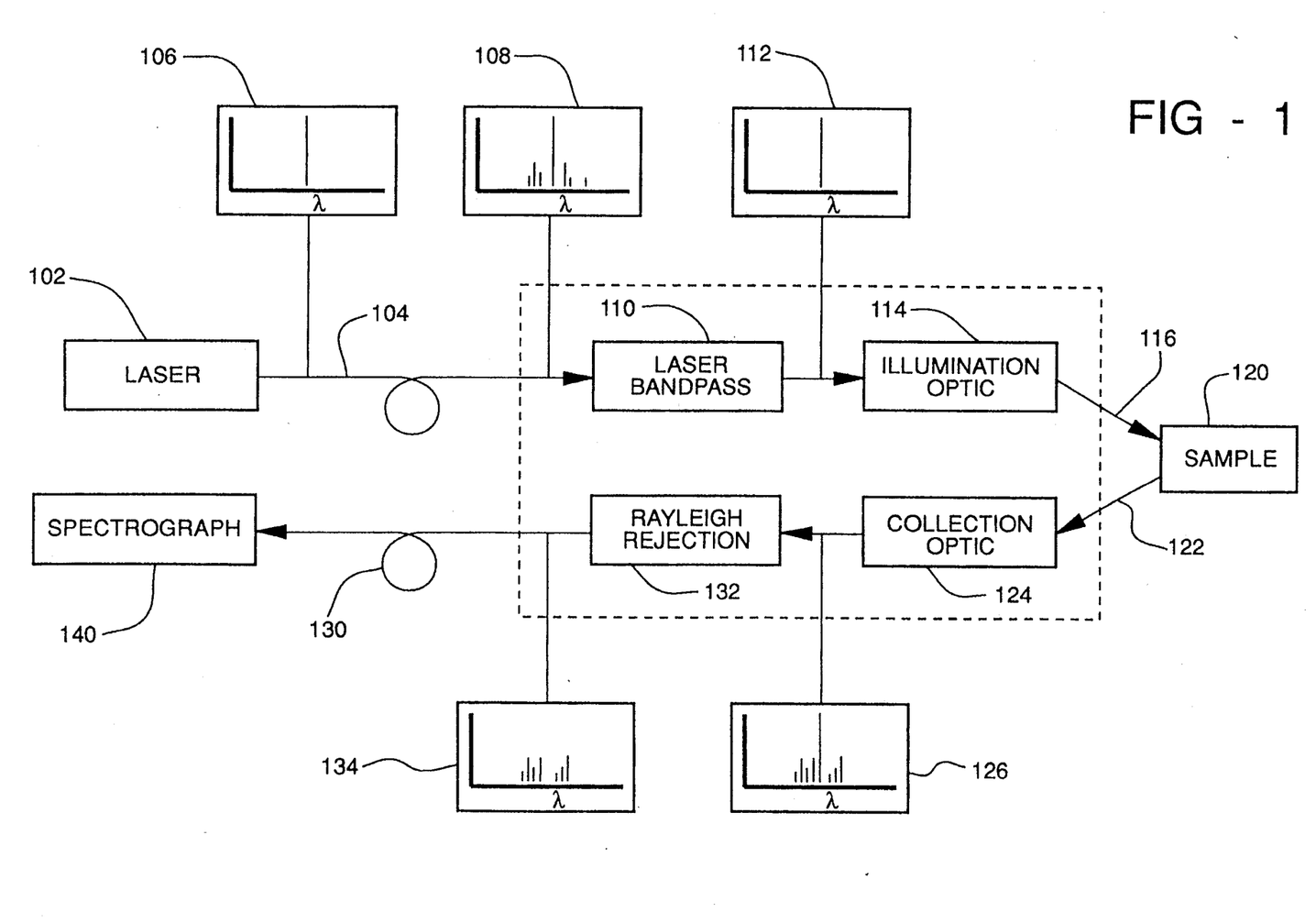
FIG. 1 is a block diagram which depicts schematically the functional elements of a remote Raman spectroscopy system and the spectral content of the optical energy present at various points therewithin.

Referring to the block diagram in FIG. 1, the functional elements of a remote Raman spectroscopy system are schematically illustrated along with the spectral content of the optical energy present at various points along the illumination and collection paths. Energy from an excitation laser 102 is coupled into the illumination fiber 104, beginning as a relatively pure, single wavelength of light as illustrated by the graph 106, which plots intensity as a function of wave number. Upon traversing fiber 104, the laser energy induces Raman scattering within the fiber material, typically composed of silica, yielding a spectrum 108 at the output of the illumination fiber which contains spurious Raman lines in addition to the laser wavelength.

Unless these undesired lines are eliminated from the illumination path before reaching the sample, their Rayleigh scatter at the sample may be indistinguishable from the true, shifted Raman scatter due to the laser excitation of the sample. Therefore, a laser band pass device 110 is used to remove these unwanted wavelengths, thereby outputting, ideally, the single laser line shown in graph 112 to the illumination optic 114 and sample under characterization 120 along path 116. It is assumed for the purposes of this discussion that illumination optic 114 contains a sufficiently short optical path that it does not itself generate significant spurious scattering.

The light scattered by sample 120, depicted by line 122, is collected by collection optic 124. At the output of collection optic 124, as depicted in graph 126, the scattered radiation consists of the unshifted Rayleigh scatter at the laser wavelength and the shifted Raman scatter that characterizes the sample 120 under test. Since the Rayleigh scatter is several orders of magnitude stronger than the Raman scatter, if allowed to enter collection fiber 130, this strong Rayleigh scatter can excite spurious Raman scattering within collection fiber 130 similar to this situation within illumination fiber 104.

This Rayleigh scatter must therefore be rejected before being coupled to collection fiber 130. This may be accomplished with a Rayleigh rejection element 132, which generates the spectra depicted in graph 134, now devoid of the strong Rayleigh line. The collection fiber 130 then conducts only the relatively weak Raman scattering lines, as depicted in graph 134, from sample 120 to an analysis instrument such as spectrograph 140 for detection.

The apparatus of Carrabba et al, U.S. Pat. No. 5,112,127 teaches such a fiber-optic probe useful for measuring Raman spectra of a sample disposed remotely from a light source and detector. This probe head contains optical components which selectively remove unwanted scattering arising from the interaction between the excitation source radiation and the input optical fiber, as previously described, while filtering the Raman excitation source into a return optical fiber leading to a spectrometer or detector.

While effective in certain applications, this prior-art probe includes several inefficiencies in design which limit overall sensitivity and resolution. One drawback concerns the fact that the strong illumination path is substantially in line with the sample, with the weaker radiation of interest being "folded" out of this path. Due to this geometry, the Carrabba probe necessarily relies upon a primary filter in the form of a narrowband transmission element to pass the laser excitation light in one direction and to reflect the Raman signal from its backside. Such an arrangement is prone to inaccuracy for several reasons, the foremost being that this primary filter is called upon to reflect a wide range of desired spectra. With practical filters, however, the efficiency of this reflection varies with wave number. As such, some wavelengths will be attenuated more than others, resulting in an overall signature exhibiting lines of unreliable magnitude. Moreover, this geometry precludes the use of more efficient and accurate optical devices associated with beam redirection and filtering.

SUMMARY OF THE INVENTION

The present invention modifies and improves upon this prior-art probe geometry, thereby allowing the use of more efficient optical components, including, in the preferred embodiments, holographic optical elements. In contrast to the configuration described above, a substantially in-line collection path is instead used, with the stronger illumination energy being "folded" into this return path. This improved arrangement of optical paths facilitates the use of a primary narrowband reflective element instead of a transmission element. This primary narrowband reflector is preferably a holographic optical element (HOE), since other available types of narrowband optical reflectors, including dielectric, rugate or other Bragg-effect types, currently do not offer the superior efficiency afforded by an HOE.

In the present invention, this narrowband reflective element not only folds the laser energy into a common sample illumination/collection optic, but also serves to reject a substantial portion of the Rayleigh scattering received from the sample. Since the reflection of a narrow band of wavelengths is much easier to control and improve than with transmission, this arrangement simultaneously reflects significantly more laser excitation light than a transmission element will pass, while transmitting more of the scattered signal than a transmission element will reflect, particularly those signals close to the excitation wavelength.

Additionally, folding of the illumination energy into an in-line collection path facilitates the use of a dispersive element, preferably another HOE, in the illumination path to remove spurious scattering generated within the fiber from the excitation source. Such a highly efficient dispersive filtering element cannot be used in a configuration having the relatively weak spectra of interest folded out of an in-line illumination path. The use of a dispersive element also allows the use of spatial filters which may take advantage of apertures in the form of pinholes or slits in the illumination or sample path as a means to remove all but the laser energy.

A holographic notch filter may be inserted into the collection path of the present invention between the narrowband reflective element and the return optical fiber, this notch filter being operative to further remove Rayleigh scatter from the scattered spectra. Additionally, beam redirection means may be provided so that the illumination and collection fibers may be substantially parallel to one another at their interface to the probe proper, thereby resulting in a more compact assembly. Preferably, a holographic transmission grating is utilized as this beam-redirecting device in the illumination path, thereby performing an additional function of excitation prefiltering before the primary filtering performed by the narrowband reflective element.

In other embodiments, a holographic beam splitter may be used as the means to redirect the illumination radiation, thus providing an alternative approach to laser light prefiltering. In further alternative embodiments, a holographic notch filter may be used as the narrowband reflective element, in which case the illumination path redirection means may take the form, of another holographic notch filter or a holographic transmission or reflection grating. Mirrors or prisms may also be used advantageously in the illumination path, depending upon the desired final geometry.

In order to observe a process flow as opposed to direct sample illumination, a light-conductive element may be added between the probe and the environment under characterization, be it liquid, gaseous, plasma, etc. Preferably, this element is composed of a material which does not produce an unwanted signature, for example a nonsilica material such as fluorite.

BRIEF DESCRIPTION OF THE DRAWINGS

FIGS. 4A through 4E depict schematic alternative embodiments of the present invention, wherein:

DETAILED DESCRIPTION OF THE INVENTION

Figure 2:
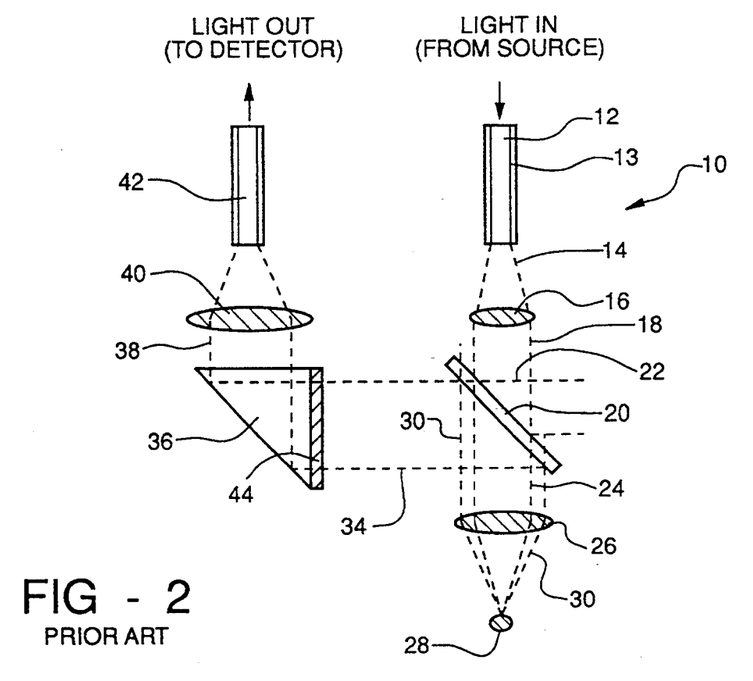
FIG. 2 is a cross-sectional illustration of a prior-art apparatus for measuring Raman spectra over optical fibers.

Having discussed the system block diagram of FIG. 1 previously in relation to the background of the invention, the reader's attention is now turned to FIG. 2, which shows a prior-art apparatus for measuring Raman spectra over optical fibers, this probe being taught by Carrabba et al in U.S. Pat. No. 5,112,127. In this prior-art device, a primary optical filter 20 is positioned in a substantially in-line path from a first optical fiber 12 carrying excitation energy to a sample 28. This primary optical filter is tuned to transmit laser excitation wavelengths while rejecting light of other wavelengths generated within this first optical fiber by the excitation light. Collimated, scattered light from sample 28 impinges onto the back face of this angled primary optical filter 20, which is further operative to transmit excitation light while reflecting the remaining light at approximately 90°, this reflective light containing the desired Raman spectrum.

In this prior-art device, the relatively strong excitation energy is delivered straight through a substantially in-line illumination path, impinging upon a sample, and then the desired, scattered energy is "folded" out of this illumination path and into a collection path, where it is subjected to beam redirecting elements and filters, resulting in a probe head optical assembly having a geometric configuration which allows the input and output fibers to be collinear and connected to the proximal end of the probe while the sample is illuminated from the distal end of the probe head.

It would be advantageous and more efficient, however, to have the stronger illumination energy folded into a substantially in-line collection path. This is true for several reasons. Firstly, such a geometry allows a narrowband reflective element to be utilized as a "primary filter." From a practical standpoint, it is much easier to tailor an optical device to efficiently and accurately filter a narrow band of wavelengths instead of a wide range of wavelengths, as required in the prior-art probe described earlier. Secondly, folding of the illumination energy into the collection path facilitates the use of a dispersive element, preferably another HOE, in the illumination path along with spatial filters to remove spurious scattering generated within the fiber from the excitation source. Such dispersive elements and attendant spatial filtering cannot be used in a configuration wherein the relatively weak spectra of interest are folded out of an in-line illumination path.

The present invention narrowband reflective element is preferably holographically recorded, since alternative dielectric, and rugate, Bragg-effect constructions are inferior in performance, at least at present. A narrowband HOE reflector simultaneously reflects more laser excitation light than the prior-art transmission element will pass, while, in the opposite direction, transmits more Raman signal than the prior-art transmission element will reflect, particularly those wavelengths close to the excitation wavelength. With an HOE in this improved optical path geometry, more laser energy may be imparted to a sample and more of the unshifted Rayleigh scattering may be excluded from the return signal, resulting in a cleaner, more accurate and higher resolution reading.

Figure 3A:
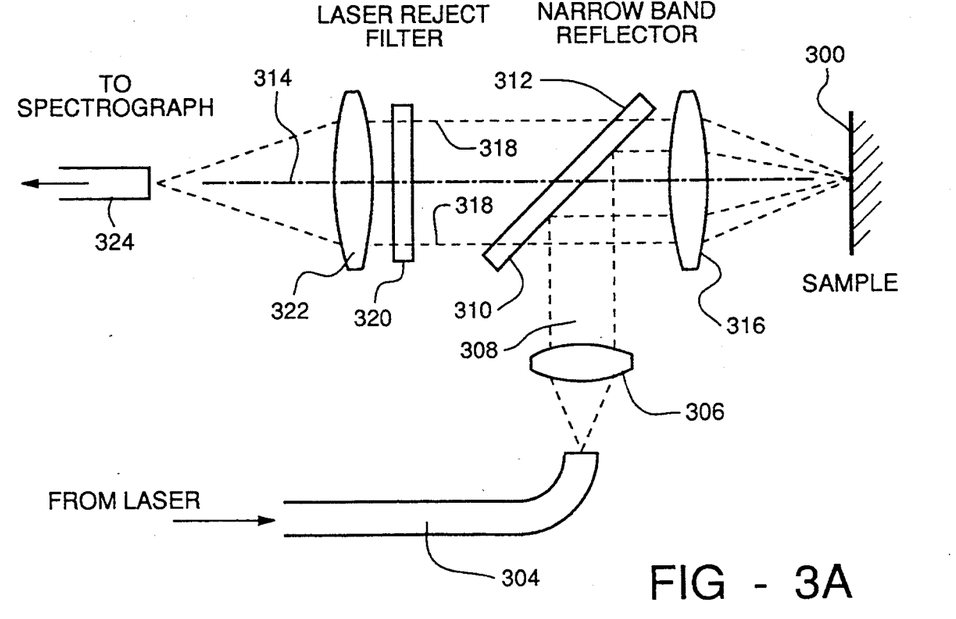
FIG. 3A is a cross-sectional illustration of a geometry for bringing excitation laser energy to a primary narrowband reflective element in accordance with the present invention.
Figure 3B:
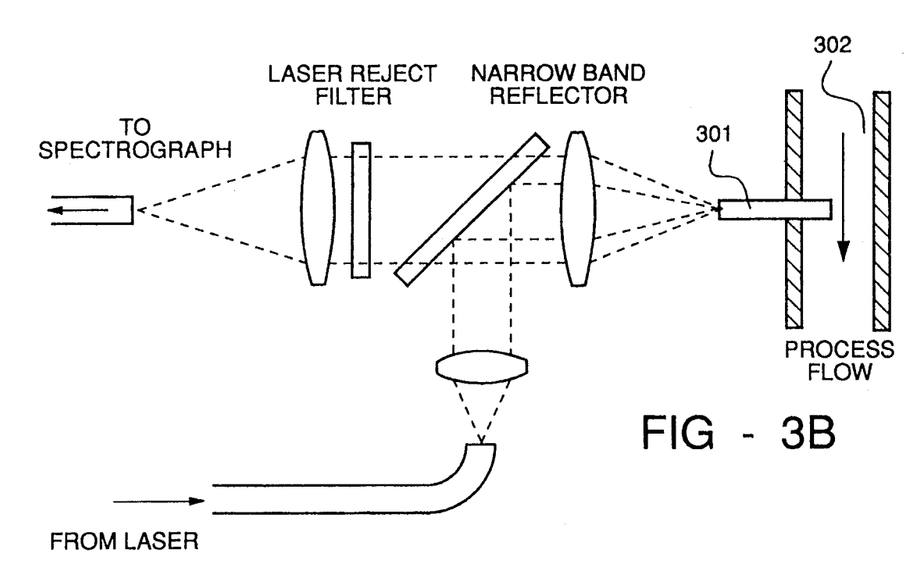
FIG. 3B shows a substantially similar geometry to that depicted in FIG. 3A, adding a relatively short, light-conductive element which mat be inserted into a process-related environment.

Now making reference to FIG. 3, there is shown a geometry of optical components formed in accordance with the present invention, this geometry being used in FIG. 3A for direct characterization of the sample 300, and in FIG. 3B, with an optional light-conductive element 301 being introduced into a process pipe 302 wherein a liquid, gas, or plasma may be present in a process-control related application. This light-conductive element may be any type of fiber or tube exhibiting light-piping properties though, preferably, this element is constructed of a material which does not introduce a strong scattering of its own. A nonsilica material may be useful in this application, including a fluorite element such as those currently available from Galileo Electro-Optics Corp. of Sturbridge, Mass.

The geometries of FIGS. 3A and 3B being substantially identical except for light-conductive element 301, the elements of FIG. 3A will,be described with the understanding that such description applies equally well to FIG. 3B. In FIG. 3A, excitation energy from a remotely disposed laser (not shown) is coupled to an illumination fiber 304. The output of this fiber, being divergent, is collimated by laser input optic 306, the collimated beam 308 impinging upon a narrowband reflector 312, which folds the laser excitation energy into the collection path, substantially in-line along axis 314.

Sample optic 316 focuses the laser excitation energy onto sample 300 and collimates the scattered radiation received therefrom along axis 314 and through reflector 312. Thus, in this capacity, narrowband reflector 312 serves four purposes; to fold the laser excitation into the substantially in-line collection path, to transmit substantially all wavelengths except those associated with the desired excitation, to pass the scattered spectra for analysis, and to reflect the strong Rayleigh signature scattered by the sample.

Many or all of the optical elements referenced herein, including HOEs such as the one preferably employed as narrowband reflector 312, may be disposed between glass surfaces with an anti-reflective (AR) coating or wedged relative to the optical element. For example, in FIG. 3A, narrowband reflector 312 may incorporate coatings or wedged surfaces in order to prevent surface reflections from being directed along axis 314. Alternatively, the optical elements may be encased in prisms in an effort to avoid such reflections.

Continuing the reference to FIG. 3A, once the desired Raman-signature-containing energy represented by lines 318 is passed through narrowband reflector 312, a laser rejection filter 320 may optionally be placed in this path to further inhibit Rayleigh scatter from being focused by output optic 322 and coupled into a second fiber 324 which carries the signal to an analysis instrument such as a spectrograph. In the embodiments shown in FIGS. 3A and 3B, the fiber 304 carrying the excitation laser energy is curved. Although this may be less desirable from a packaging standpoint, it uses a minimum number of optical components in the resulting probe.

Figure 4A:
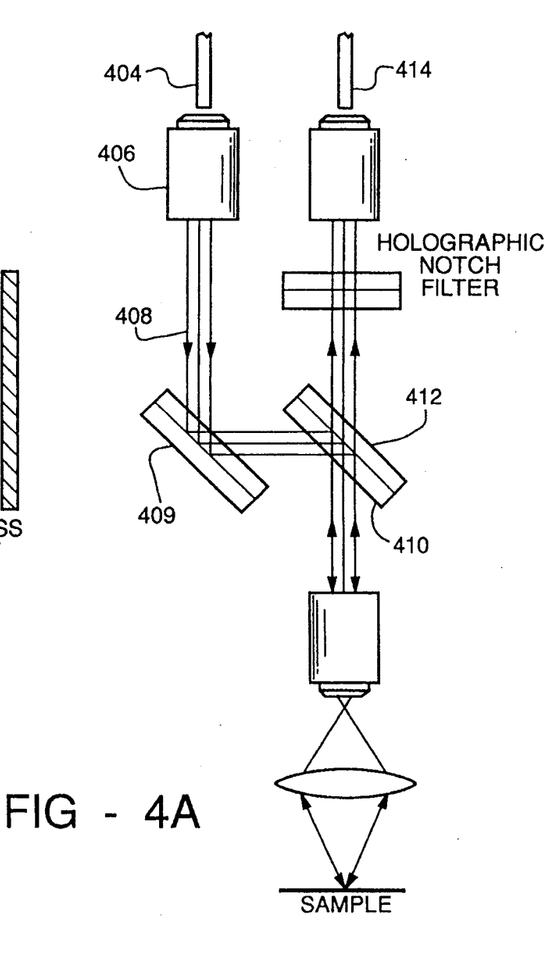
FIG. 4A uses a holographic beam splitter to redirect and filter the illumination path.

Now referencing FIG. 4A, an alternative embodiment is shown wherein an input fiber 404 from a laser impinges upon optic 406, the collimated beam 408 being redirected by a reflective device 409 in order to strike surface 410 of narrowband reflector 412. Reflective device 409 may be a mirror, a right-angle prism or a similar or identical narrowband reflector such as device 412. A second narrowband reflector used as device 409 provides additional attenuation of spurious Raman scattering generated within fiber 404 to ensure that such undesirable excitation does not reach the sample. The types of demanding applications which might require the use of a second narrowband reflector include those involving very long length fibers, very low Raman,signal levels, and/or lower-performance primary narrowband reflectors situated at position 412 in FIG. 4A. Mention may also be made of the fact that with a reflective element 409, input fiber 404 and output fiber 414 may resultingly be parallel to one another, this geometry being preferred in a probe requiring a narrower width dimension.

Figures 4B, 4C:
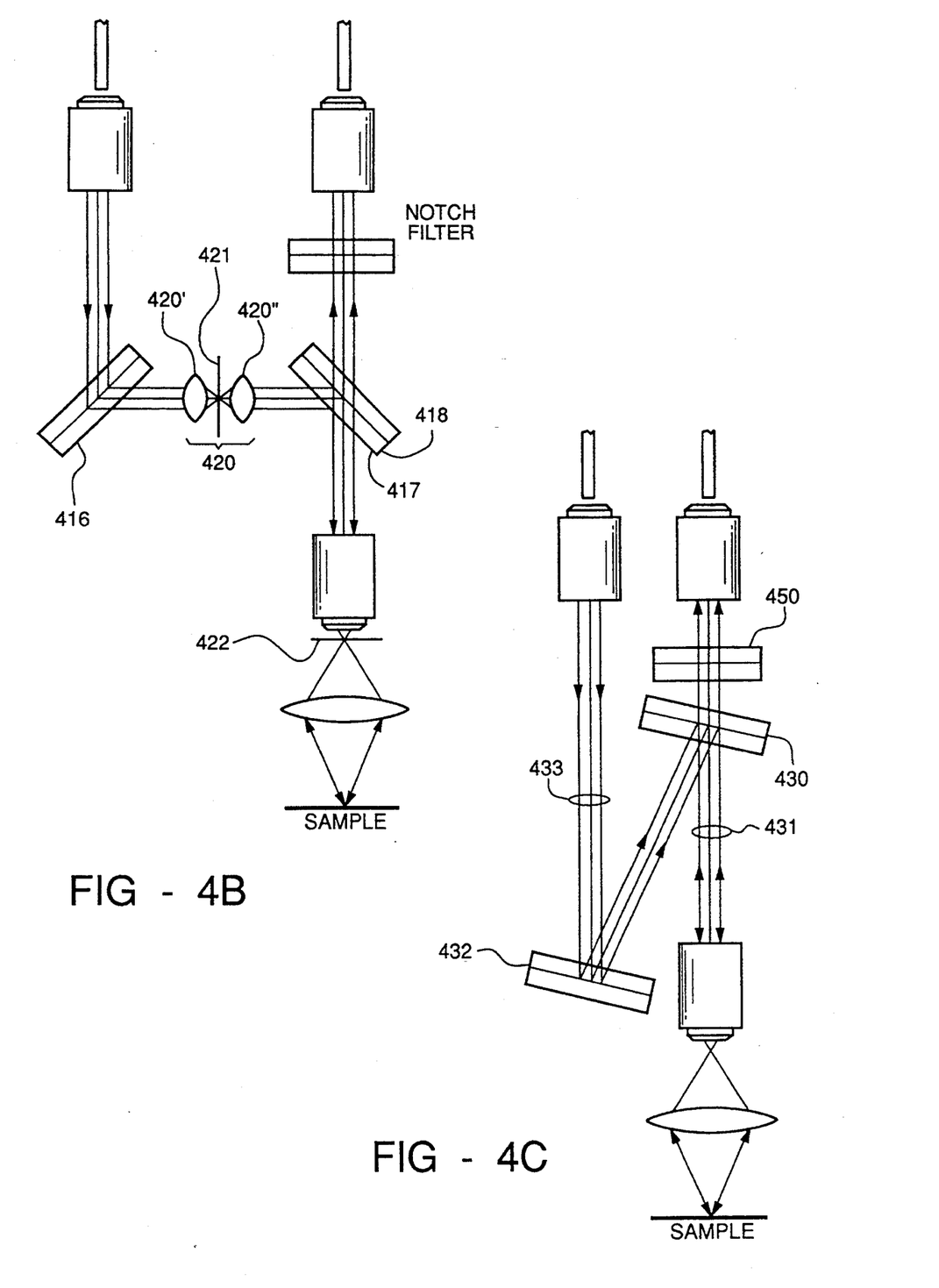
FIG. 4B uses a holographic transmission grating to redirect and filter the illumination path, wherein further filtering is provided by a spatial filter, and with a pinhole or slit associated with the sample end to improve focusing.
FIG. 4C uses a holographic notch filter in the illumination path and in the collection path, these filters being slightly off axis with respect to the substantially in-line collection path.

In FIG. 4B, there is shown an alternative embodiment wherein the laser excitation energy is redirected by means a dispersive element, in this case a transmission grating 416. This grating, preferably holographically produced, functions to diffract the laser wavelength to the primary narrowband reflector 418. Unwanted wavelengths are either transmitted harmlessly through grating 416 to an absorbing surface (not shown) or, if diffracted, are angularly separated from the primary illumination and collection paths. With such angular dispersion being used as an excitation energy separation technique, spatial filtering may advantageously used to further reject non-laser wavelengths. For example, spatial filter 420 may be positioned between holographic transmission grating 416 and the primary reflective element 418, the filter 420 including an input optic 420' which focuses the incoming illumination energy through a pinhole or slit formed in the surface represented by line 421, and an output lens 420" which recollimates the beam. A pinhole or slit represented by line 422 may also placed at the focal point of the optic associated with the delivery of excitation illumination to the sample and with the collimation of the scattered radiation received therefrom. With either arrangement, only wavelengths substantially close to the excitation wavelength received through the dispersive element are allowed to illuminate the sample.

FIG. 4C shows yet another alternative embodiment of the present invention, wherein the narrowband reflective element is a primary holographic notch filter 430 which is incorporated into the substantially in-line collection path 431, this primary notch filter being fed by a second holographic notch filter 432 used to redirect and filter the illumination energy along path 433. In this embodiment, the preferred notch filter is a holographically produced Supernotch ™ filter manufactured by Kaiser Optical Systems Inc., which allows the collection of Stokes and anti-Stokes data within 50 wavenumbers of the laser line without the need to readjust the filter angle.

As in all of the embodiments described thus far, a narrowband notch filter 450 is also shown in the collection path to further reject Rayleigh scattering from the sample at the laser wavelength to prevent this scattering from again exciting Raman scattering within the collection fiber where it may compete with the desired Raman signal from the sample. This filter may be any type of Rayleigh-rejection filter, such as a holographic notch filter, holographic edge filter, dielectric stack, or of the rugate variety. Holographic notch filters are again the preferred choice, though in certain applications involving either low Rayleigh scatter coefficients at the sample or short fiber probe lengths, this additional Rayleigh filtering may either be unnecessary or may be adequately provided at the spectrograph input.

Figures 4D, 4E:
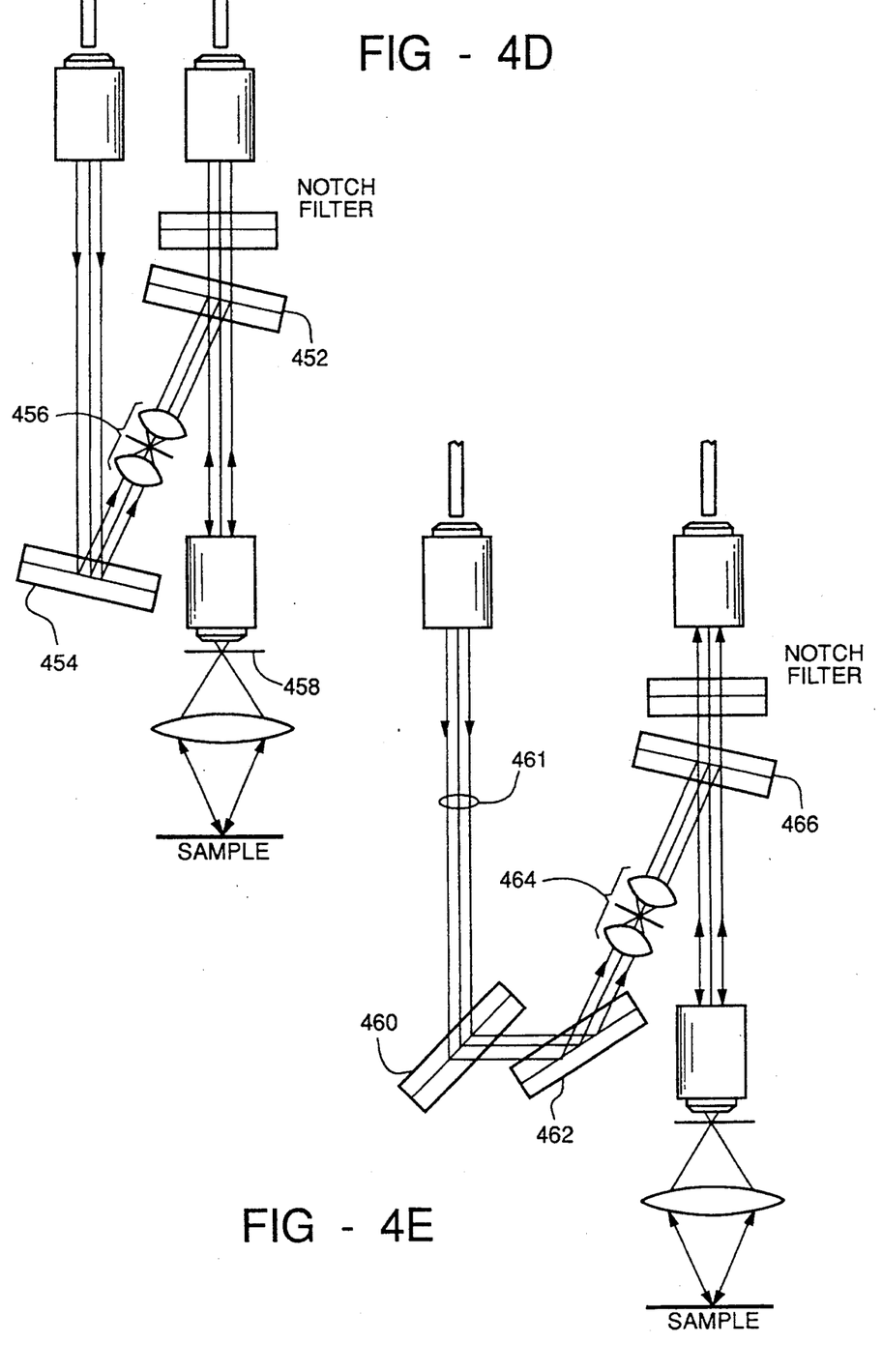
FIG. 4D retains the holographic notch filter in the collection path as in FIG. 4C, but in this case a holographic reflection grating is placed in the illumination path and used to feed the primary notch filter, a spatial filter optionally being included between the reflection grating and the notch filter to filter the laser energy.
FIG. 4E uses a holographic transmission grating and a mirror to redirect energy along the illumination path to a primary holographic notch filter situated in the collection path, with an optional spatial filter being used between the mirror and the notch filter.

FIG. 4D illustrates yet another alternative embodiment of the present invention. In this case a primary holographic notch filter 452 is again used in the collection path, but the holographic notch filter 432 in FIG. 4C has been replaced with a holographic reflection grating 454 to redirect the illumination energy. Again, due to the fact that dispersion is used to separate the desired laser wavelength from unwanted illumination, a spatial filter 456 is preferably, yet optionally, incorporated. An additional option includes a pinhole or slit 458 positioned within the optic associated with the sample end of the probe, the use of this aperture being delineated previously.

In FIG. 4E, there is shown yet another alternative embodiment of the present invention, in which a holographic transmission grating 460 is used to redirect illumination beam 461 to a mirror 462, through a spatial filter 464, and onto a primary narrowband reflector in the form of holographic notch filter 466. Due to the fact that transmission grating 460, spatial filter 464 and holographic notch filter 466 may all work in combination to remove non-laser wavelengths from the illumination path, the embodiment depicted in FIG. 4E is intended for those applications demanding perhaps the most rigorous wavelength control. Moreover, mirror 462 may, itself, be replaced by a narrowband reflector providing even further attenuation of non-laser wavelengths.

In terms of physical construction, the various components associated with the present invention probe are preferably housed in an enclosure proximate to a sample under characterization, preferably with the illumination and collection fibers being attached on or through the proximal end of the enclosure and with the sample optic supported toward the distal end of the enclosure. The fibers are preferably parallel to one another, though various other geometries are possible, including the incorporation of the probe components within a microscope body, in which case the microscope objective lens may conveniently be used as the sample optic.

Having thus described our invention, we claim:

1. A probe for measuring an optical effect remotely wherein a first optical fiber is used to carry excitation energy to the probe and a second optical fiber is used to carry scattered radiation from the probe for spectral analysis, the probe comprising:
   an input optic for receiving excitation energy from the first optical fiber;
   a sample optic to deliver the excitation energy to a sample under characterization and to receive radiation scattered therefrom;
   an output optic for coupling the scattered radiation to the second optical fiber;
   the optical path between the sample optic and the output optic defining a substantially in-line collection path within the probe;
   a narrowband reflective element disposed in the collection path, the element being operative to:
   (a) receive the excitation energy from the input optic by way of an illumination path and fold the energy into the collection path for delivery to the sample through the sample optic, and
   (b) reject from the collection path a substantial portion of Rayleigh scattering received from the sample through the sample optic; and
   a dispersive element disposed in the illumination path to direct excitation energy onto the narrowband reflective element.

2. The probe of claim 1 further including a spatial filter in the illumination path to further reject wavelengths other than the wavelength associated with the excitation energy.

3. The probe of claim 2 wherein the spatial filter is disposed between the dispersive element and the narrowband reflective element in the collection path.

4. The probe of claim 2 wherein the spatial filter is disposed proximate to a focal point of the sample optic.

5. The probe of claim 2 wherein the spatial filter includes an aperture in the form of a pinhole or a slit.

6. A probe for measuring an optical effect remotely wherein a first optical fiber is used to carry excitation energy to the probe and a second optical fiber is used to carry scattered radiation from the probe for spectral analysis, the probe comprising:
   an input optic for receiving excitation energy from the first optical fiber;
   a sample optic to deliver the excitation energy to a sample under characterization and to receive radiation scattered therefrom;
   an output optic for coupling the scattered radiation to the second optical fiber;
   the optical path between the sample optic and the output optic defining a substantially in-line collection path within the probe;
   a holographic notch filter disposed in the collection path, the filter being operative to:
   (a) receive the excitation energy from the input optic by way of an illumination path and fold the energy into the collection path for delivery to the sample through the sample optic, and
   (b) reject from the collection path a substantial portion of Rayleigh scattering received from the sample through the sample optic; and
   a beam re-directing device disposed in the illumination path to direct excitation energy onto the holographic notch filter.

7. The probe of claim 6 wherein the beam re-directing device is a holographic notch filter.

8. The probe of claim 6 wherein the beam re-directing device is a dispersive element.

9. The probe of claim 8 further including a spatial filter in the illumination path to further reject wavelengths other than the wavelength associated with the excitation energy.

10. The probe of claim 9 wherein the spatial filter is disposed between the beam re-directing device and the holographic notch filter in the collection path.

11. The probe of claim 9 wherein the spatial filter is disposed proximate to a focal point of the sample optic.

12. A probe for performing an optical measurement on a sample at a remote location wherein a first optical fiber is used to carry excitation energy to the remote location and a second optical fiber is used to carry scattered radiation away from the remote location, the probe comprising:

an enclosure;

an input optic associated with receiving excitation energy from the first optical fiber;

a sample optic associated with delivering the excitation energy to the sample and to receive radiation scattered therefrom;

an output optic associated with coupling the scattered radiation to the second optical fiber, the optical path within the enclosure between the sample optic and the output optic being a substantially in-line, collimated collection path;

a holographically recorded optical element to reflect a narrow band of wavelengths associated with the excitation energy while substantially transmitting all other wavelengths, the optical element being operative to:

(a) fold the narrow band of wavelengths into the collection path for delivery to the sample through the sample optic, and (b) fold out of the collection path any Rayleigh scattering received from the sample through the sample optic; and a dispersive optical device disposed in the illumination path to direct excitation energy onto the narrowband reflective element.

13. The probe of claim 12 wherein the enclosure constitutes a portion of the volume within a microscope body, and wherein the sample optic makes use of the microscope objective lens.

* * * * *